United States Patent [19]

Sloane

[11] Patent Number: 5,298,604
[45] Date of Patent: Mar. 29, 1994

[54] PARITAL PRIMARY AMINO ACID SEQUENCE OF THE ANTINEOPLASTIC PROTEIN (ANUP); A CYTOKINE PRESENT IN GRANULOCYTES

[76] Inventor: Nathan H. Sloane, 1842 Brookside Dr., Germantown, Tenn. 38138

[21] Appl. No.: 116,539

[22] Filed: Sep. 2, 1993

Related U.S. Application Data

[63] Continuation of Ser. No. 919,885, Jul. 27, 1992.

[51] Int. Cl.$^5$ .............................................. C07K 15/12
[52] U.S. Cl. .................................... 530/351; 530/350; 530/380
[58] Field of Search ..................... 530/380, 350, 351

[56] References Cited

U.S. PATENT DOCUMENTS

| | | | |
|---|---|---|---|
| 4,359,415 | 11/1982 | Sloane | 530/395 |
| 4,559,325 | 12/1985 | Burzynski | 530/834 X |
| 5,008,372 | 4/1991 | Wellner | 436/90 |

OTHER PUBLICATIONS

Sloane et al. Biochemical Journal (1986), 234, pp. 355–362.
Pottahil et al, Cancer Therapy and Control (1990), 1, pp. 193–198.
Sloane et al, FASEB Journal (1991), 5 A546, Abstract #1019.

*Primary Examiner*—Howard E. Schain
*Attorney, Agent, or Firm*—Longacre & White

[57] ABSTRACT

Electrophoretically homogeneous human Antineoplastic Urinary Protein (ANUP) contains a blocked N-terminal amino acid that has been identified as pyroglutamic acid. Removal of the pyroglutamy residue by the use of pyroglutamyl aminopeptidose results in the formation of the deblocked protein which is also an antineoplastic molecule. The amino acid sequence of the deblocked ANUP 16 KD monomer showed the following sequence:

Cycle No.
 1. Leu L
 2. Lys K
 3. Cys C
 4. Tyr Y
 5. Thr T
 6. Cys C
 7. Lys K
 8. Glu E
 9. Pro P
 10. Met M Cycle No.
 11. Thr T
 12. Thr (T)? or Ser (S)?
 13. Ala A
 14. Ala A
 15. X?

A data base search using the above sequence showed that 100% homology with another protein was not found regardless of unassigned positions.

The blocked N-terminal amino acid of ANUP is pyroglutamic acid.

2 Claims, No Drawings

PARTIAL PRIMARY AMINO ACID SEQUENCE OF THE ANTINEOPLASTIC PROTEIN (ANUP); A CYTOKINE PRESENT IN GRANULOCYTES

This is a file wrapper continuation application of U.S. Ser. No. 07/919,885, filed Jul. 27, 1992.

BACKGROUND OF INVENTION

Field of the Invention

The present invention relates to the partial primary amino acid sequence of the N-terminal amino acids of ANUP after removal of the N-terminal pyroglutamyl residue. This antitumor cytokine is present in human granulocytes and is excreted from the serum into the urine, since the protein is also present in the serum.

Generally in accordance with the present invention, the electrophoretically homogeneous ANUP (monomer 16 KD) is treated with pyroglutamyl aminopeptidase to liberate the free N-terminal amino group. The deblocked protein is transblotted and the amino acid sequence of the electrophoretically homogeneous deblocked protein is determined.

SUMMARY OF THE INVENTION

The present invention describes the elucidation of the partial N-terminal amino acid sequence of ANUP; the protein (ANUP) contains a blocked N-terminal amino acid; this blocking amino acid has been identified as a pyroglutamyl residue and upon its removal by pyroglutamyl aminopeptidase the free N-terminal amino acid is exposed for sequencing.

DESCRIPTION OF THE PREFERRED EMBODIMENT

Immunoaffinity Chromatographic Purification of ANUP

After silica gel ($SiO_2$) adsorption of ANUP from urine, the adsorbent is washed with cold $H_2O$ and the protein is eluted with cold dilute ammonia (pH 9-10). The eluate is concentrated (after neutralization) utilizing an Amicon UM 20 Diaflo membrane. The concentrate is dialyzed against cold $H_2O$ and adjusted to pH 8.0 after the addition of 0.1M Tris-0.5M NaCl. The solution at pH 8 is applied to an immunoaffinity column containing rabbit ANUP antibody (IgG fraction), Sloane, et al., Biochemical Journal (1986) 234, 355-362, U.S. Pat. No. 4,359,415, Sloane Nov. 16, 1982). The antibody (IgG fraction) is coupled to CH-Sepharose 4B containing a 6 carbon-COOH side arm. After 24 hours at 4° the column is washed with buffer followed by an $H_2O$ wash. The protein is eluted by washing the column with 0.1M Tris-0.9% NaCl at pH 2.5. The eluate is neutralized and dialyzed before freeze-drying. The yield of pure ANUP is 100-200 ug/liter.

Purification of ANUP after Dissociation of Florisil Eluate into Monomer Subunits Pure ANUP contains aggregates of monomeric units ±16 KD as shown by Sloane, et al., Biochemical Journal (1986) 234, 355-362 (SDS-PAGE) electrophoresis and ultracentrifugal studies. Therefore, direct filtration of the neutralized dialyzed $SiO_2$ eluate adjusted to pH 8.8 with 0.1% SDS-glycine-Tris (0.1M) buffer and incubated at room temperature allows dissociation of the protein into monomer units that can pass through the UM 20 Amicon Diaflo membrane. This filtrate neutralized and dialyzed yields about 100-200 ug pure ANUP per liter.

Preparation of ±16 KD ANUP Protein Band by Polyacrylamide Gel Electrophoresis in the Presence of 0.1% Sodium Dodecyl Sulfate (SDS-PAGE)

The flat bed SDS-PAGE gel lanes are loaded with approximately 15 ug of ANUP per lane with protein marker lane as control. The ±16 KD ANUP band is cut from the gels, and the gel bands are homogenized in Freunds complete adjuvant for injection into rabbits to prepare antibodies as described below under "Preparation of AntiANUP."

Preparation of AntiANUP

The gammaglobulin fraction of antiANUP is prepared after immunizing rabbits with electrophoretically homogeneous protein; the preparation of the protein fraction is described under heading "Preparation of 16 KD ANUP."

The rabbits are injected initially at multiple sites in the back and in the thigh muscles with the SDS-PAGE gel homogenate (16 KD) utilizing a 10% polyacrylamide gel containing 0.1% sodium dodecyl sulfate (SDS) and mercaptoethanol as described by Laemmli [Nature (London) (1970) 680-685].

The initial immunization contains complete Freunds adjuvant, approximately 200 ug protein in 0.5 ml (SDS-PAGE) 16K are mixed with 0.5 ml of complete Freunds adjuvant and thoroughly homogenized; 0.1 ml are subcutaneously injected into each rabbit and 0.3 ml of the homogenate are injected in each of the thigh muscles. The immunization regimen (with the exception of multiple site injections) is repeated three times at 2-3 week intervals using incomplete Freunds adjuvant. Two weeks after the third incomplete Freunds adjuvant injection, the rabbits are bled. The blood is allowed to clot, and the antiserum is collected. The gammaglobulin fraction $0.5_s$ ammonium sulfate precipitate is collected by centrifugation, washed with 50% saturated ammonium sulfate, and the precipitate is suspended in distilled water and dialyzed against water to remove salts. The salt-free fraction is then dried from the frozen state and the yield is approximately 1 g per 100 ml of antiserum.

Coupling of AntiANUP Gammaglobulin to CH-Sepharose 4B with 6 Carbon COOH Side Arm 6 grams of CH-Sepharose 4B with a 6 carbon COOH side arm (Pharmacia Fine Chemicals AB, Uppsals, Sweden) are washed with 1200 ml of 0.5M NaCl for 1 hour on sintered glass funnel. The gel is added to 390 mg of antiANUP gammaglobulin (IgG) then 50 ml $H_2O$ are added and the pH adjusted to 6.0; the coupling reagent 1-ethyl-3-(3-dimethylamine propyl) carbodiimide-HCl is then added; the pH is adjusted to 4.9; the mixture is shaken at room temperature (end over end) for 24 hours. The pH is readjusted to 4.9 after shaking for 30 minutes, 60 minutes, 120 minutes and 20 hours. The coupled gel is poured into a 1.9 cm diameter chromatographic column and washed at 4° with 0.1M borate buffer-1M NaCl (pH 8.0) to $H_2O$ and then washed with $H_2O$, followed by a wash of 0.1M glycine-1.0M NaCl (pH 2.5) and finally washed with $H_2O$; this cycle treatment is repeated three times. Finally the column is washed with 0.1M Tris-0.5M NaCl pH 8.0 containing 0.04% sodium azide.

Determination of the Partial N-terminal Amino Acid Sequence

The N-terminal sequence of the ANUP has been shown to be blocked by a pyroglutamate residue. The conclusion of this result has been shown by the following:

L-leucine aminopeptidase treatment of the UM 20 ANUP Amicon filtrate activity did not affect the antineoplastic activity, thus indicating that the N-terminal protein was blocked. The protein was incubated at room temperature for 24 hours in the 0.1% SDS-glycine, pH 8 before subjecting the solution to filtration through the Amicon UM 20 membrane. The protein (in the filtrate) showed upon PAGE (pH 8 with 0.1% SDS) a single protein peak with a molecular weight of about 44K. Thus, the immunoaffinity purified ANUP dissociated into the low molecular weight protein was reassociated to the trimeric form; occasionally a single protein peak of (tetramer) was observed upon PAGE as previously reported by Sloane, et al. (1986).

Treatment of the UM 20 filtrate (ANUP) with pyroglutamate aminopeptidase removed the N-terminal pyroglutamic acid. The protein after treatment with pyroglutamate aminopeptidase still showed antineoplastic activity; thus, the removal of N-terminal pyroglutamate residue did not affect the biological activity. However, the antineoplastic activity of the pyroglutamate aminopeptidase digest of the treat protein (free of the N-terminal pyroglutamate) was completely destroyed by digestion with L-leucine aminopeptidase. Thus, these experiments proved that the blocked N-terminal pyroglutamate protein is resistant to the proteolytic action of L-leucine aminopeptidase; and, furthermore, upon the removal of the N-terminal pyroglutamate (which is not essential for biological activity), the free N-terminal protein can then be digested by leucine aminopeptidase to a biologically inactive material.

Pyroglutamate Aminopeptidase Treatment of ANUP

ANUP 0.88 u moles (16 KD monomer) dissolve in 4 ml $K_xH_xPo_4$ buffer at pH 7.4.

Add 0.74 mg. disodium ethylene diamine tetracetic acid (EDTA).

Add 0.3 mg. dithiotreitol.

Add 27 mU pyroglutamate amino peptidase (Boehinger).

Flush tube with nitrogen.

Cap tube and incubate at 30° for 18 hours.

Digestion with L-leucine Aminopeptidase of ANUP Predigested with Pyroglutamate Aminopeptidase a. Deblocked ANUP (UM 20 filtrate) (predigested with pyroglutamate aminopeptidase) (3.5 mg) 9.22 u mols adjusted to pH 8.5 with Tris (1 ml total volume)

b. 1 mg of L-leucine aminopeptidase (Sigma, Type V) equivalent to 100 units was added, and the mixture incubated at 37° for 1 hour.

c. The mixture was dialyzed at 4° C. against phosphate buffered saline.

d. The digest was assayed for biological (antitumor) activity.

TABLE 1

Digestion of ANUP with L-leucine Aminopeptidase Predigested with Pyroglutamate Aminopeptidase and Assayed for Antitumor Activity

| | | Antitumor activity ug/unit* |
|---|---|---|
| 1. | Treatment with leucine aminopeptidase | 0.40 |
| 2. | Leu aminopeptidase digestion | 0.40 |
| 3. | Control no treatment ANUP | 0.40 |
| 4. | Pyrogluatamate aminopeptidase digestion | 0.40 |
| 5. | Treatment with pyroglutamate aminopeptidase followed by treatment with leucine aminopeptidase | no antitumor activity |

*Unit equals the concentration for 50% growth inhibition per ml.

An alternate method for the preparation of highly purified ANUP by the differential Amicon Diaflo membrane involves filtrations of the $SiO_2$ eluate after $(NH_4)_2 SO_4$ precipitation and passage through an immunoaffinity column containing antiurokinase IgG, bound to CH-Sepharose 4B as described above. The pass solution from the immunoaffinity column is then dialyzed and lyophilized; the yield is 4 mg protein per liter of urine.

The protein concentrate is dissolved in 0.1% SDS-glycine buffer at pH 8.8 and the solution is incubated at 37° for 24 hours before filtration through a YM 30 Amicon Diaflo membrane; the filtrate containing ANUP is cooled to 4° and adjusted to pH 4.2 and set at 4° for 24 hours. This solution is then concentrated utilizing YM 30 Amicon Diaflo filtration at 4°. The concentrate is dialyzed against cold $H_2O$ and lyophilized. The yield of highly purified ANUP is 200 ug per liter.

Purification of the Pyroglutamate Digest

PAGE Analysis of the YM 30 filtrate shows essentially a single 16 KD monomer (silver strain).

The 16 KD monomer is then treated with pyroglutamate aminopeptidase to remove the pyroglutamyl residue and expose a free N-terminal amino acid. Prior to sequencing the deblocked protein is purified by the electroblotting technique after PAGE analysis and electroblotting the ±16 KD protein band. The amino acid sequence is performed on this electroblotted protein band. The N-terminal amino acid sequence is as follows (all L-amino acids):

leucinyl-lysinyl-cysteinyl-tyrosinyl-threoninyl-cysteinyl-lysinyl-glutamyl-prolinyl-methioninyl-threoninyl-threoninyl or serinyl-alaninyl-alaninyl . . . .

L-K-C-Y-T-C-K-E-P-M-T-(T or S)-A-A

Biological Properties of ANUP

ANUP inhibits the growth and kills the human tumor cell lines-HeLa (human cervical tumor cell line), CALU-6 (human lung tumor cells), SW 1990 (human pancreas tumor cells) and HL 60 (human leukemia cells). The protein does not affect the growth of human diploid cells nor the growth of the mouse or hamster tumor cell lines. The protein does not affect the growth of human diploid cell lines WI 38 and HF 54.

This antitumor protein (ANUP) may be utilized as a potential antitumor chemotherapeutic agent to treat human neoplastic disease. This view of potential use of ANUP in cancer therapy is justified by the following:

a) ANUP is non-toxic to human cells;

b) ANUP specifically inhibits only human cancer cell lines;

c) ANUP causes regression of human tumor cell lines implanted in nude mice.

I claim:

1. Deblocked Antineoplastic Urinary Protein (ANUP) for producing pharmacological antitumor activity, said deblocked ANUP having a partial free N-terminal L-amino acid sequence comprising:

leucinyl-lysinyl-cysteinyl-tyrosinyl-threoninyl-cysteinyl-lysinyl-glutamyl-prolinyl-methioninyl-threoninyl-threoninyl-alaninyl-alaninyl . . . .

2. Deblocked Antineoplastic Urinary Protein (ANUP) for producing pharmacological antitumor activity, said deblocked ANUP having a partial free N-terminal L-amino acid sequence comprising:

leucinyl-lysinyl-cysteinyl-tyrosinyl-threoninyl-cysteinyl-lysinyl-glutamyl-prolinyl-methioninyl-threoninyl-serinyl-alaninyl-alaninyl . . . .

* * * * *